United States Patent [19]

Manabe

[11] 4,311,394
[45] Jan. 19, 1982

[54] AUTOMATIC ANALYTICAL APPARATUS

[75] Inventor: Sugio Manabe, Kodaira, Japan

[73] Assignee: Olympus Optical Company Limited, Tokyo, Japan

[21] Appl. No.: 138,518

[22] Filed: Apr. 9, 1980

[30] Foreign Application Priority Data

Apr. 12, 1979 [JP] Japan .................................. 54-44735

[51] Int. Cl.³ .......................................... G01N 21/00
[52] U.S. Cl. ...................... 356/440; 356/39; 356/434; 422/64
[58] Field of Search ................ 356/39, 425, 434, 440; 422/63, 64

[56] References Cited

U.S. PATENT DOCUMENTS 3,847,486 11/1974 McCabe ............................. 356/434
3,966,322 6/1976 Greaves et al. ...................... 356/39
4,063,816 12/1977 Itoi et al. ............................. 356/434

Primary Examiner—R. A. Rosenberger

[57] ABSTRACT

An automatic analytical apparatus for effecting quantitative analysis of a given substance contained in a sample such as blood, urine or the like and comprising a sample holding and carrying means including a plurality of sample holding positions and operative to carry the sample held by one of the sample holding positions more than one round along a closed loop, a photometric means fitted to a given position of the closed loop and operative to effect at least two photometric operations, a transfer means for transferring one sample to the sample holding position without transferring any other sample to the latter, and a discarding means operative to discard the sample only which has been subjected to the given number of photometric operations.

5 Claims, 2 Drawing Figures

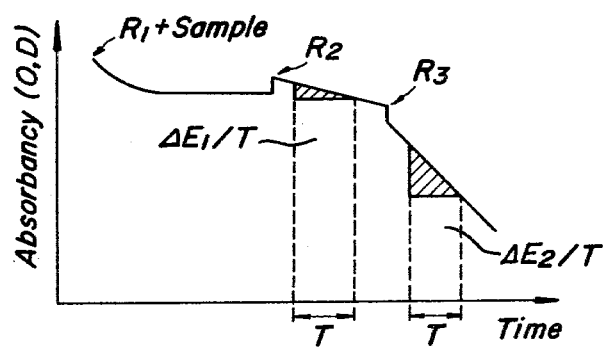
FIG_2

AUTOMATIC ANALYTICAL APPARATUS

BACKGROUND OF THE INVENTION

1. Field of the Invention

This invention relates to an automatic analytical apparatus for effecting quantitative analysis of a given substance contained in a sample such as blood, urine or the like.

2. Description of the Prior Art

Various kinds of automatic analytical apparatus for measuring the reaction speed of a sample and effecting quantitative analysis of a given substance contained therein have heretofore been proposed. In one of the conventional automatic analytical apparatus, provision is made of two photometric means distant apart from each other and arranged along a reaction line of a sample to be carried at a given period. A difference between absorbancies measured by these two photometric means is detected to measure the reaction speed of the sample. Then, the quantitative analysis of a desirous substance contained in the sample is effected on the basis of the reaction speed thus measured. However, the use of these two photometric means for the purpose of obtaining the change in absorbancy measured by each photometric means provides the disadvantage that the characteristic of a photometric optical system comprising a light source, photoelectric converting element or the like must be adjusted such that the characteristic of the photometric optical system of one of the photometric means is equal to that of the other photometric means, and as a result, each photometric means is complex in construction, and that the use of the two photometric means makes the apparatus as a whole large in size and expensive.

Another automatic analytical apparatus which makes use of a centrifuge system for the purpose of effecting a plurality of photometric operations of the same sample by means of the same photometric means has also been proposed. This conventional apparatus is provided with a disc rotor having a plurality of sets of depressions and a sample is delivered from a delivering means into the depression and then the disc rotor is driven by a centrifuge. After a lapse of several seconds, the sample is transferred through respective holes provided at the outside wall of the depression to the photometric means where the plurality of photometric operations of the sample are effected. But, such apparatus has the disadvantage that the disc rotor must be replaced by a new one everytime the photometric operation is effected and hence is troublesome in operation, and that it is impossible to simultaneously measure a number of items.

SUMMARY OF THE INVENTION

An object of the invention, therefore, is to provide an automatic analytical apparatus which can eliminate the above mentioned drawbacks which have been encountered with the prior art techniques and which is simple in construction and small in size and which can effect analysis as to a number of items in a rapid and efficient manner.

A feature of the invention is the provision of an automatic analytical apparatus for effecting quantitative analysis of a sample as to the substance to be analyzed, characterized by comprising a sample holding and carrying means including a plurality of sample holding positions arranged along a closed loop at a given pitch for carrying said sample holding positions at a given period, a photometric means fitted to a given position of the loop of the sample holding and carrying means and effecting successive photometric operations of the samples carried in succession, a discarding means for selectively discarding the sample held by said sample holding position, a sample transfer means for transferring successive samples to each sample holding position of said sample holding and carrying means at a given transfer position thereof at a given period which is slower than said period of carrying said sample holding position along said closed loop, whereby during the time at which the sample held by one of the sample holding positions is carried more than one round along the loop by means of said sample holding and carrying means, said photometric means is operative to effect at least two photometric operations without transferring the other samples to said sample holding position and said discarding means is operative to discard the sample only which has been subjected to said given number of photometric operations.

Further objects and features of the invention will be fully understood from the following detailed description with reference to the accompanying drawings, wherein:

BRIEF DESCRIPTION OF THE DRAWINGS

FIG. 2 is a graph illustrating change in absorbancy in which error due to reactions other than those being measured is eliminated.

DETAILED DESCRIPTION OF THE PREFERRED EMBODIMENTS

Figure 1:
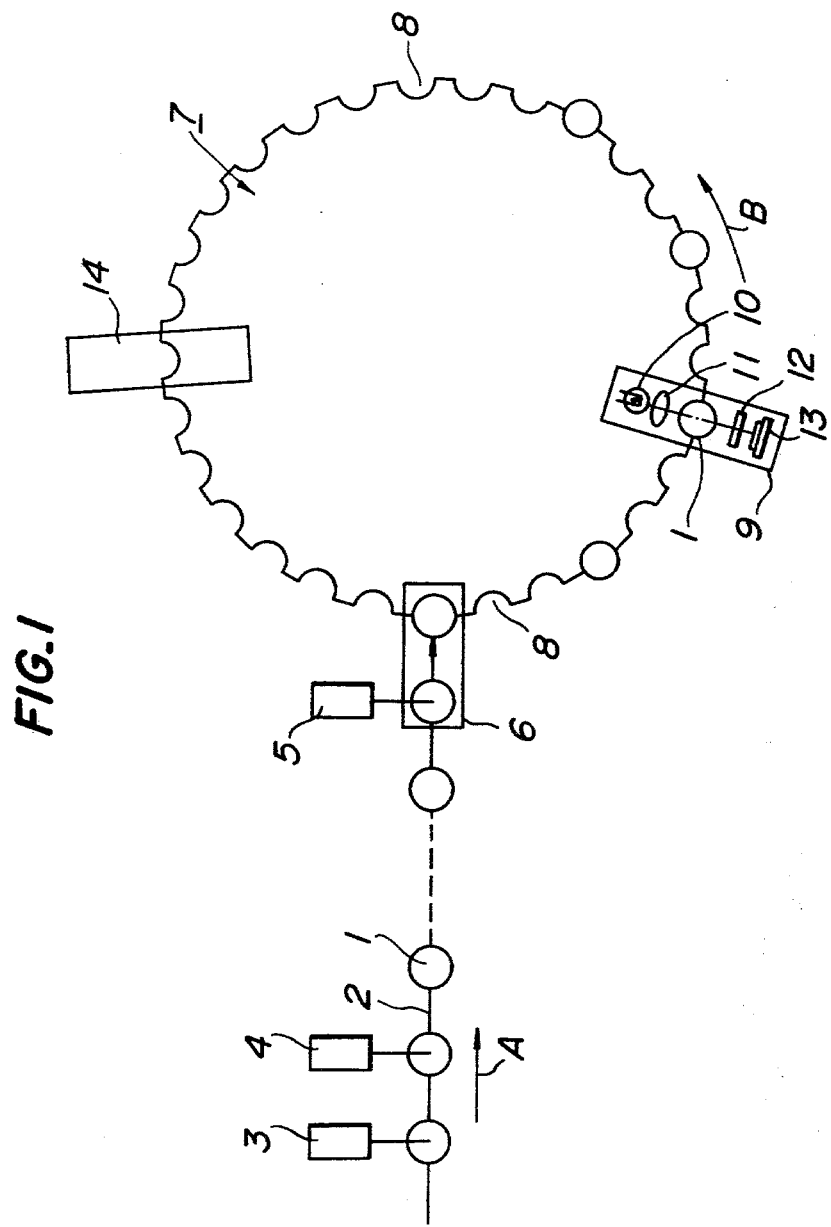
FIG. 1 is a diagrammatic view of one embodiment of an automatic analytical apparatus according to the invention.

FIG. 1 shows one embodiment of an automatic analytical apparatus according to the invention. A cuvette 1 is held by a cuvette carrying mechanism 2 and intermittently carried along a rectilinear reaction line shown by an arrow A at a of 6 seconds. Near the reaction line A is arranged a sample delivering means 3 which functions to attract each of the samples from a sampler mechanism (not shown) operative to hold containers that enclose various kinds of samples extracted therein and carry the sample container, the sample thus attracted being delivered into the cuvette 1. As viewed in the reaction line A, in front of the sample delivery means 3 are arranged two reagent delivery means 4, 5 operative to selectively deliver a reagent corresponding to the substance to be analyzed from a plurality of containers (not shown) to the sample containing cuvette 1.

At the end of the reaction line A is arranged a cuvette transfer means 6 operative to transfer a sample to which a given reagent has been added together with the cuvette 1 to a cuvette holding and carrying means 7. In the present embodiment, the cuvette holding and carrying means 7 is composed of 29 cuvette holding positions 8 equidistantly spaced apart from each other on the same circumference and operative to be intermittently rotated along a photometric line shown by an arrow B at a period of 2 seconds which is faster than the cuvette carrying period. The cuvette holding and carrying means 7 is provided at its one position with a photometric means 9 operative to pass the cuvette 1 held by the cuvette holding position 8 therethrough and measure the absorbancy of the sample enclosed in the cuvette. In the present embodiment, the photometric means 9 is composed of a polychromatic light source 10, a lens 11 for changing a light emitted from the light source 10 into a parallel light flux, a space corresponding to the cuvette 1, an interference filter 12 operative to change over the light transmitted through the cuvette 1 according to the substances to be analyzed and cause a light having a specified wave length to pass therethrough, and a photoelectric converter element 13 for receiving the light passed through the interference filter 12. The cuvette holding and carrying means 7 is provided at the other position with a cuvette discarding means 14 operative to selectively discard the sample together with the cuvette 1 after the given light measurement of the sample has been completed.

The analytical operation of the automatic analytical apparatus shown in FIG. 1 will now be described.

The cuvette 1 on the reaction line A is carried to the photometric line B at a period of 6 seconds. The photometric line B operates at a period of 2 seconds. As a result, the cuvette 1 successively carried along the reaction line A is held by every third cuvette holding position 8 of the photometric line B by means of the cuvette transfer means 6. As a result, the earliest cuvette 1 held by the cuvette holding position 8 passes through the photometric means 9 three times at a 58 seconds interval until the cuvettes 1 are held by all of the 28 cuvette holding positions 8. In this case, if the difference between the absorbancies at respective time intervals of each cuvette 1 on the photometric line B is obtained, it is possible to effect the quantitative analysis of the desired substance contained in each sample on the basis of the reaction speed. In the case of effecting three photometric operations of each sample, it is possible to measure the difference between the absorbancies of each test liquid two times. The analytical result can be obtained by selecting an average value of the differences between absorbancies or selecting either one of the differences between the absorbancies, for example, and by calculating on the basis of the reaction speed thereof. That cuvette 1 which has completed three photometric operations as given is selectively discarded from the cuvette holding position 8 by means of the cuvette discarding means 14 at that position of the cuvette holding and carrying means 7 which is short of the position where the cuvette holding and carrying means 7 arrives at the cuvette transfer means 6. In this way, it is possible to hold the cuvette 1, to be transferred successively from the reaction line A to the cuvette holding and carrying means 7 by means of the cuvette transfer means 6, by the cuvette holding position 8 of the cuvette holding and carrying means 7 without overlapping the successive cuvettes on the cuvette holding position 8.

The automatic analytical apparatus shown in FIG. 1 is capable of using only one photometric means 9 for the purpose of effecting a plurality of photometric operations of each sample and detecting the difference between absorbancies. As a result, if use is made of a plurality of photometric means, it is not necessary to adjust the mutual relation between adjacent photometric means. As a result, the automatic analytical apparatus shown in FIG. 1 is simple in construction and small in size. In addition, even when the reaction line A and photometric line B are of a single line, respectively, each kind of sample can be analyzed with respect to different items. In addition, the speed of carrying the cuvette 1 in the photometric line B is made higher than that in the reaction line A and hence the cuvette 1 can be transferred from the reaction line A to the photometric line B without overlapping the cuvette 1 on the cuvette holding position 8 of the cuvette holding and carrying means 7. As a result, the automatic analytical apparatus shown in FIG. 1 has a sufficiently high treating ability even when the apparatus as a whole in size. As in the case of the conventional automatic analytical apparatus, if the photometric operation is effected at the reaction line A, the feeding speed of the sample must be determined in correspondence with the time intervals for producing a difference between the absorbancies. As a result, in order to obtain an excellent treating ability, it is necessary to make the photometric interval long, thereby accelerating the feeding speed of the sample. In this case, however, even though the treating ability is improved, the photometric interval on the reaction line A is long, so that it is inevitable that the apparatus becauses large in size and that each photometric means becomes complex in construction.

Another embodiment of an automatic analytical apparatus according to the invention will now be described.

In the embodiment shown in FIG. 1 the sample on the reaction line A together with each cuvette 1 is transferred to and held by the cuvette holding position 8 of the cuvette holding and carrying means 7 by means of the transfer means 6. Alternatively, the cuvettes may be mounted beforehand on each cuvette holding position 8 and the sample only on the reaction line A may be transferred to the cuvette by means of a sample delivering means fitted to a given position of the loop of the sample holding and carrying means and delivering the sample to successive cuvettes mounted beforehand on each sample holding position. Moreover, the cuvette transfer means 6 shown in FIG. 1 may be replaced by a delivering means for transferring the sample only to the photometric line B and by a discarding means for discarding the cuvette whose sample has been transferred to the photometric line B. In addition, the cuvette discarding means 14 on the cuvette holding and carrying means 7 may be replaced by a cuvette cleaning and discarding means for selectively cleaning and discarding the cuvette which has been subjected to the given number of photometric operations.

Alternatively, the absorbancy may be measured at the end point where the reaction of the sample has been completed so as to effect the quantitative analysis of any desired substance. In this case, each sample passes through the photometric means 9 shown in FIG. 1 three times, so that the interference filter 12 is changed over everytime the photometric operation is effected and hence it is possible to effect an analysis in a highly reliable manner by means of a compound wave length method. In addition, if two photometric operations of the test liquid are effected and the quantitative analysis is effected by the two wave length method, it is possible to discard the cuvette after the two photometric operations have been completed and correct the drift of the apparatus in the case of effecting the third photometric operation. In this way, if the drift of the apparatus is corrected by means of the optical system which is the same as that which is used for effecting the photometric operation, it is possible to effect the analysis in a highly precise manner. In order to analyze different measurement items of various kinds of samples at the point where the reaction of the test liquid is completed, use must be made of a member of interference filters which can transmit lights having different wave lengths. In this case, provision is made of a plurality of photometric means each including equally divided interference filters which are operative to be selectively changed over concerning each test liquid. Even when provision is made of a plurality of photometric means, if the above mentioned drift correction is effected by means of each photometric means, it is not necessary to effect the mutual matching between these photometric means. As a result, the apparatus becomes simple in construction.

In addition, provision may be made of means for selectively delivering a given reagent to the cuvette 1 on the photometric line B shown in FIG. 1 so as to continuously measure direct bilirubin and total bilirubin or separate the reactions other than the reaction belonging to the substance to be analyzed and effect the blank correction and measure GOT (Glutamic Oxaloacetic Transaminase) from the reaction speed. That is, heretofore it has been the common practice to measure the direct bilirubin and total bilirubin with the aid of independent channels. As a result, the measurement required twice as much sample and reagent. On the contrary, if another reagent delivering means is arranged on the photometric line B, in the first place, it is possible to mix the sample and diazo reagent on the reaction line A and then the mixture thus obtained is subjected to one photometric operation on the photometric line B to measure the direct bilirubin. Subsequently, methanol is delivered to the cuvette with the aid of the independent reagent delivering means on the photometric line B and the photometric operation is again effected to effect continuous photometric operation of total bilirubin. The use of such measure provides the important advantage that the amount of sample and reagent becomes small, and that the indirect bilirubin can simply be obtained by calculating the difference between the total bilirubin and the direct bilirubin thus measured. In addition, in the case of measuring GOT from the reaction speed, heretofore it has been the common practice to deliver $R_1$ (conjugate enzyme, coferment, buffer solution) and $R_3$ (substrate liquid) to the sample and the sample thus delivered with $R_1$, $R_3$ is heated and then $R_2$ (substrate liquid) is added thereto. Subsequently, the change in absorbancy is measured to obtain the activity value. In this case, various ingredients contained in the sample induced reactions other than those belonging to the substances to be analyzed, and as a result, it was not always possible to effect a highly precise quantitative analysis. On the contrary, if provision is made of independent reagent delivering means on the photometric line B shown in FIG. 1, it is possible to eliminate the cause of error due to reactions other than those belonging to the substance to be analyzed by a stepwise measurement process and hence to effect a highly precise analysis.

That is, as shown in FIG. 2, R, is added to the sample on the reaction line and heated and then $R_2$ is added. Subsequently, the sample is subjected to two photometric operations on the photometric line B to measure the change in absorbancy $\Delta E_1$. $R_3$ is now added to the sample from the independent reagent delivering means on the photometric line B. Subsequently, the change in absorbancy $\Delta E_2$ is again measured to obtain ($\Delta E_2$-$\Delta E_1$). As a result, four photometric operations in total are effected and it is possible to obtain the change in absorbancy from which is eliminated the error due to reactions other than those belonging to the substance to be analyzed. Alternatively, $R_2$ may be added to the sample on the photometric line B.

Let it be assumed that the carrying step H of the cuvette 1 on the reaction line A shown in FIG. 1 is 6 seconds, that the carrying step S of the cuvette 1 on the photometric line B is 2 seconds, that the number of the photometric opetations N is 3, and that the number of the cuvette holding positions 8, that is, the total number T of the cuvettes 1 on the photometric line B is 29, the cuvette transfer means 6 is capable of successively transferring the cuvette 1 from the reaction line A to the cuvette holding portion 8 of the cuvette holding and carrying means 7 without overlapping the cuvette 1 one upon the other, thereby effecting the desired number of photometric operations. The above mentioned H, S, N and T may be changed, but must satisfy the following conditions, i.e.

$$N = H/S$$

$$T = C \cdot N + K$$

where $H > S$, N is a positive integer which is larger than 2, C is a positive integer exclusive of 0, K is an integer of $1, 2, \ldots, (N-1)$, prime numbers common to both $|T - C \cdot N|$ and N being excluded by factoring $|T - C \cdot N|$ and N into prime numbers.

For example, let $N = 6$ and $C = 1$, then T is given by $$T = 7, 8, 9, 10, 11.$$

But, if $|T - C \cdot N|$ and N are factored into prime numbers so as to exclude the prime numbers common to both $|T - C \cdot N|$ and N, then the integer of K is given by 1 or 5. As a result, T is given by $$T = 7 \text{ or}$$

$$T = 11.$$

In addition, H and S may be determined to any value under the condition that $H/S = 6$.

In the embodiment shown in FIG. 1, the photometric line B is made circular in shape. But, the photometric line B may take any desired shape provided that the photometric line B is of closed loop.

As stated hereinbefore, the automatic analytical apparatus according to the invention is simple in construction and small in size and can effect analysis of many items in a rapid and efficient manner.

What is claimed is:

1. An automatic analytical apparatus for effecting quantitative analysis of given substances in samples comprising cuvette carrying means for carrying cuvettes successively along a reaction line at a first period H to a sample transferring position;

sample holding and carrying means including a plurality of sample holding positions arranged along a closed loop at a given pitch and carrying said sample holding positions at a second period S through said sample transferring position, a photometering position and a sample discarding position in this order, said second period S being shorter than said first period H;

sample transfer means arranged at said sample transfering position for transferring successively samples contained in the successive cuvettes which are successively fed into said sample transferring positions by said cuvette carrying means, into the sample holding position of the sample holding and carrying means;

photometric means arranged at said photometering position for effecting photometric operation for the samples held and carried by said sample holding and carrying means; and discarding means arranged at said sample discarding position for discharging the samples out of the sample holding positions of the sample holding and carrying means after the respective samples in the sample holding and carrying means have been fed along said closed loop by more than one round during which the respective samples have been passed through said photometric means more than twice to effect the photometric operation for the respective samples more than twice; whereby the first period H, the second period S and the number T of sample holding positions of the sample holding and carrying means are so determined that each of the samples successively carried at the sample transferring position can be transferred into vacant sample holding positions.

2. The apparatus according to claim 1 wherein said sample transfer means comprises a sample delivering mechanism for delivering the samples contained in the cuvettes successively arriving at said sample transferring position, into given cuvettes mounted beforehand at the sample holding positions of the sample holding and carrying means.

3. The apparatus according the claim 1, wherein said sample transfer means comprises a cuvette transfer mechanism for transferring the sample containing cuvettes successively arriving at said sample delivering position, into given sample holding positions of the sample holding and carrying means.

4. The apparatus according to claim 1, wherein said sample holding and carrying means further comprises a reagent delivering position on said closed loop at which position is arranged a reagent delivering mechanism for delivering a given reagent to eliminate cause of error due to reactions other than those belonging to a given substance to be analyzed.

5. The apparatus according to claim 1, wherein the first carrying period H of the cuvettes along the reaction line, the second carrying period S of the samples along the closed loop and the total number T of the sample holding positions of the sample holding and carrying means are determined to satisfy the conditions given by $$N = H/S \text{ and}$$

$$T = C \cdot N + K$$

wherein $H > S$, N is a positive integer larger than 2, C is a positive integer exclusive of 0, and K is an integer of 1, 2, ..., (N−1), excluding values of K where $|T - C \cdot N|$ and N have at least one common prime number other than unity.

* * * * *